United States Patent [19]

Takahashi et al.

[11] Patent Number: 4,714,566
[45] Date of Patent: * Dec. 22, 1987

[54] PROCESS FOR PRODUCING W/O/W TYPE MULTIPLE EMUSION

[75] Inventors: Yasuyuki Takahashi; Shigeru Aizawa; Shigeru Tamai; Toshiro Yoshida; Takeshi Takahashi, all of Tokyo, Japan

[73] Assignee: Meiji Milk Products Company Limited, Tokyo, Japan

[*] Notice: The portion of the term of this patent subsequent to Dec. 2, 2003 has been disclaimed.

[21] Appl. No.: 610,465

[22] Filed: Aug. 3, 1984

[30] Foreign Application Priority Data

Mar. 2, 1984 [JP] Japan ................... 59-038667

[51] Int. Cl.$^4$ .................. B01J 13/00; B01F 17/34
[52] U.S. Cl. .................. 252/314; 252/312; 252/356; 426/602; 426/604; 514/943
[58] Field of Search .............. 252/312, 314, 356; 514/943; 426/602, 604

[56] References Cited

U.S. PATENT DOCUMENTS

| 3,232,765 | 2/1966 | Rosenthal et al. | 252/312 X |
| 3,939,290 | 2/1976 | Terada et al. | 426/602 X |
| 4,254,105 | 3/1981 | Fukuda | 514/943 X |
| 4,590,086 | 5/1986 | Takahashi et al. | 426/602 |
| 4,626,443 | 12/1986 | Takahashi et al. | 426/602 |
| 4,626,444 | 12/1986 | Takahashi et al. | 426/602 |
| 4,632,840 | 12/1986 | Takahashi et al. | 426/602 |

FOREIGN PATENT DOCUMENTS 0031709 3/1974 Japan ................... 252/312
1235667 6/1971 United Kingdom .

OTHER PUBLICATIONS

Berkman et al.: "Emulsions and Foams", Reinhold Publishing Corp., New York, 1941, pp. 60-66.

Primary Examiner—Richard D. Lovering
Attorney, Agent, or Firm—Browdy and Neimark

[57] ABSTRACT

A stable W/O/W type multiple emulsion containing very fine water droplets and suitable for use in the production of foods, cosmetics and medicines is prepared by using a glycerol unsaturated fatty acid ester as an emulsifier for a W/O emulsion.

3 Claims, 1 Drawing Figure

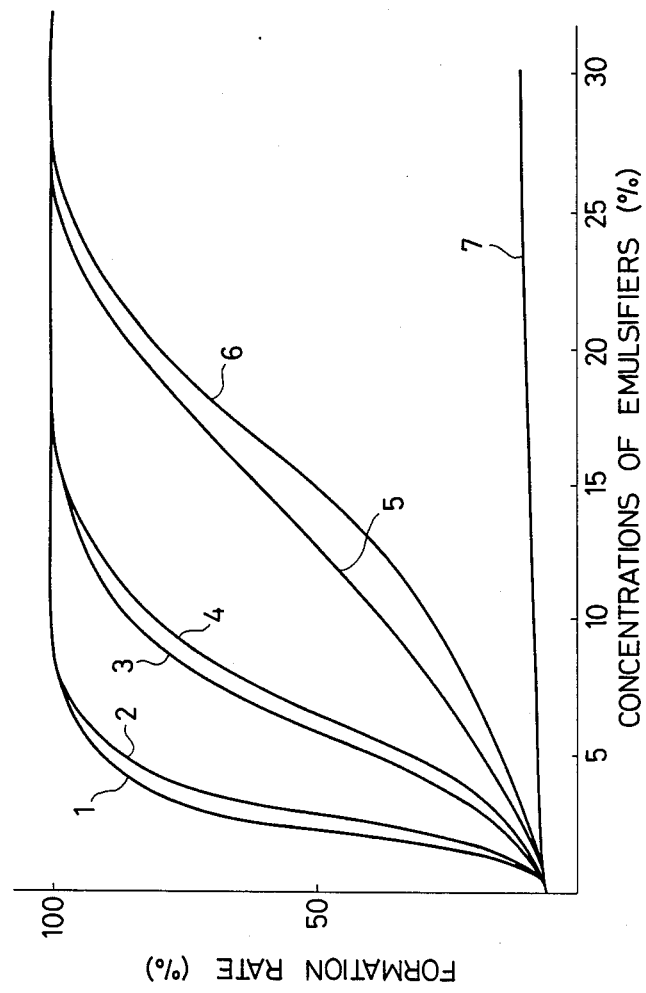

PROCESS FOR PRODUCING W/O/W TYPE MULTIPLE EMUSION

FIELD OF THE INVENTION

The present invention relates to a process for producing a quite fine W/O/W type multiple emulsion having an excellent stability.

BACKGROUND OF THE INVENTION

Generally, the use of W/O/W type multiple emulsions in the production of various cosmetics, medicines and foods have been expected, since they have a fine texture and a quite smooth touch, a watersoluble substance can be encapsulated in the fat globules in the emulsions and an apparent fat ratio can be increased.

In conventional processes for producing a W/O/W type multiple emulsion, at least 20%, based on an oil, of a Span-type emulsifier such as sorbitan monooleate is used in the primary emulsification and the resulting product is subjected to the secondary emulsification.

However, when the emulsifier is used in an amount of as large as 20% based on the oil, a taste of the emulsifier becomes strong unfavorably. The product thus obtained could not be used generally as a food.

SUMMARY OF THE INVENTION

After intensive investigations made for the purpose of finding an emulsifier capable of forming a W/O/W type multiple emulsion even when it is used in a small mount, the inventors have found a glycerol unsaturated fatty acid ester usable as the emulsifier.

The present invention provides a W/O/W type multiple emulsion quite suitable for use in the production of mayonnaises, dressings, dips, whip topping coffee whitener, imitation ice creams and drinks. Another object of the invention is to provide a process for producing rich food or low-calorie rich food having a low fat content. Still another object of the invention is to provide a W/O/W type multiple emulsion for use in the production of not only foods but also various products of emulsion types such as cosmetics and medicines.

The present invention provides a process for producing a W/O/W type multiple emulsion characterized by using a glycerol unsaturated fatty acid ester.

BRIEF DESCRIPTION OF THE DRAWING

FIG. 1 shows a relationship between W/O/W type multiple emulsion formation rate and concentrations of various emulsifiers observed in Test 1.

DETAILED DESCRIPTION OF THE INVENTION

The glycerol unsaturated fatty acid esters to be used as the emulsifier in the present invention include monoerucin, dierucin, monolinolein and dilinolein. They may be used either alone or in the form of a mixture of two or more of them.

In the process of the present invention, the emulsifier in an amount of 0.1 to 15%, preferably 1.0 to 10%, particularly 1 to 6%, based on an oil is added to the oil to obtain a mixture. The oil may be any one. In using a hardened oil, it is made molten by heating before the use. If necessary, lecithin and/or glycerol difatty acid ester may be added thereto in an amount of about 0.5 to 30% based on the emulsifier.

Water used for the production of the emulsion may contain various additives such as proteins, starches, gums, malic acid and salts thereof, organic acids and salts thereof, coloring agent and seasonings. This aqueous phase may be preheated.

In an embodiment of the process for producing the W/O/W type multiple emulsion of the present invention, the aqueous phase is added successively to the oil phase, and the obtained W/O emulsion is subjected to a phase inversion to form a W/O/W type multiple emulsion at once.

In another process of the invention, a W/O emulsion is first produced. In an embodiment of this process, the aqueous phase is added successively to the oil phase to directly obtain a W/O emulsion. In another embodiment of this process, the oil phase is added successively to the aqueous phase to obtain an O/W emulsion and then this emulsion is subjected to a phase inversion to form a W/O emulsion. According to the present invention, the W/O emulsion containing fine water droplets can be obtained by any of the above-mentioned processes. The latter phase inversion process is particularly preferred, since fine, uniform water droplets can be obtained.

In the second process based on the phase inversion, an oil containing an emulsifier is added to water or an aqueous phase successively to obtain a mixture.

To obtain a fine emulsion, it is not preferred to add a large amount of the oil at once. The oil to water ratio may be determined suitably depending on the purpose. For effecting the subsequent phase inversion sufficiently, the oil to water ratio is preferably in the range of about 3/1 to ⅓.

The thus obtained O/W emulsion is thoroughly mixed by means of a homomixer to effect the phase inversion into W/O emulsion. By the phase inversion, a quite fine, smooth emulsion can be obtained and various additives can be encapsulated in the aqueous phase in the oil. The stirring is effected preferably by means of a powerful homomixer of about 3000 to 8000 rpm. Further, an emulsifying machine such as a homogenizer or a stirring device such as a votator may also be used. It is preferred to heat the W/O emulsion to 50° to 80° C. for facilitating the subsequent emulsification.

The aqueous phase is prepared according to the present invention as follows: an additive or a mixture of additives are added to water. The additives include, for example, proteins such as casein, sodium caseinate, soybean protein, gelatin, wheat protein, plasma protein, whey protein and albumen; mucilages such as egg yolk, starch, modified starch, dextrin, cyclodextrin, starch derivatives, locust bean gum, xanthane gum, pullulan, dextran, curdlan, guar gum, tamarind gum, agar, carrageenan, furcellaran, alginic acid and salts thereof, propylene glycol alginate, pectin, arabinogalactan, crystalline cellulose, CMC, methylcellulose, acacia, tragacanth gum, karaya gum and sodium polyacrylate; as well as orthophosphoric acid, pyrophosphoric acid, polyphosphoric acid and salts of them, common salt, vinegar, organic acids and salts thereof and emulsifiers. The emulsifier may be any hydrophilic emulsifier. Further, a colorant, seasoning, etc. may be added thereto according to the purpose. The aqueous phase is preferably heated to about 50° to 80° C. so as to facilitate the emulsification. The order of the addition of the additives is not limited. For convenience sake in the operation, the W/O emulsion is charged in a stirrer and then the aqueous phase containing the emulsifier is added thereto. The stirrer herein used may be any stirrer in which the stirring blades do not impact directly the upper W/O emulsion layer, such as a stirrer having stirring blades at the bottom thereof, a suction-type stirrer having stirring blades all over the device and a stirrer for only the suction mixing.

The aqueous phase is mixed with the W/O emulsion in the stirrer at, for example, 250 rpm for 5 min and then the resulting mixture is treated in a homogenizer to obtain a quite fine W/O/W emulsion.

Thus, according to the present invention, a stable W/O/W emulsion containing extremely fine water droplets can be obtained. By using this emulsion, dense mayonnaises, dressings, dips, whip topping coffee whitener, imitation ice creams and drinks can be prepared. When the present invention is employed in the production of an emulsion-type cosmetic, the resulting cosmetic has characteristic properties of cosmetics of both W/O emulsion and O/W emulsion types. Therefore, according to the present invention, various creams and lotions having a fresh, good feeling, an extremely high spreadability and excellent cleansing effects and nutritive effects can be obtained. When the present invention is employed in the production of medicines, a physiologically active substance may be encapsulated in the inner aqueous phase to obtain a controlled-release medicine.

The following test and example will further illustrate the present invention.

Test 1

The following emulsifier was added to 300 g of hardened soybean oil heated to 50° C. in an amount of 1 to 30% (varied) based on the oil:
1. monoerucin,
2. dierucin,
3. monolinolein,
4. dilinolein,
5. glycerol monooleate,
6. glycerol dioleate,
7. glycerol monostearate.

The resulting mixture was added slowly to 200 g of water heated to 50° C. to obtain an O/W emulsion, which was then stirred by means of a homomixer at 6000 rpm to effect the phase inversion and to obtain a W/O emulsion.

500 g of water containing 1% of sodium caseinate and 2% of sorbitan monostearate was heated to 70° C. The W/O emulsion heated to 70° C. was added to the water. The resulting mixture was stirred in a stirrer having stirring blades at the bottom at 250 rpm for 5 min, then treated in a homogenizer at a rate of 100 kg/cm$^2$ and cooled to 5° C.

The W/O/W formation rate of each of the thus obtained W/O/W emulsions was examined to obtain the results shown in FIG. 1. The numerals 1 to 7 stand for the above-mentioned emulsifiers.

It is apparent from FIG. 1 that the emulsifiers 1 to 4 were particularly effective in obtaining the W/O/W emulsions.

The W/O/W type emulsion formation rate was determined according to a method of Matsumoto et al. described in "Yukagaku" 26(10), 655 (1977).

EXAMPLE 1

2900 g of hardened soybean oil was heated to 50° C. 100 g of monoerucin (monoerucic acid ester of glycerol) was added to the oil and mixed together.

Separately, 2000 g of water was heated to 5° C. and 20 ml/min of the hardened soybean mixture was added thereto under stirring with a homomixer at 6000 rpm. In the course of the addition, the O/W phase was inverted into a W/O phase to obtain 5000 g of an emulsion.

Separately, 4850 g of water, 100 g of sorbitan monostearate and 50 g of sodium caseinate were mixed together. The mixture was heated to 70° C. This mixture was charged in a stirrer having stirring blades at the bottom thereof together with the above-mentioned W/O emulsion heated to 70° C. The mixture was stirred at 250 rpm for 5 min, treated 20 at a rate of 100 kg/cm$^2$ in a homogenizer and cooled to 5° C. to obtain a W/O/W emulsion.

The resulting W/O/W emulsion was stable during the storage at ambient temperature for a quite long time.

What is claimed is:

1. A process for producing a W/O/W type multiple emulsion which comprises adding, to water or an aqueous phase, an oil phase to which 1.0 to 10% of monoerucin or dierucin is added, mixing them to form an O/W emulsion, stirring the emulsion to effect phase inversion, adding the resulting W/O emulsion to an aqueous phase, and stirring them.

2. A process for producing a W/O/W type multiple emulsion which comprises adding water or an aqueous phase to an oil phase to which 1.0 to 10% of monoerucin or dierucin is added, mixing them, adding the resulting W/O emulsion to an aqueous phase, and stirring them.

3. A process for producing a W/O/W type multiple emulsion which comprises adding water or an aqueous phase to an oil phase to which 1.0 to 10% of monoerucin or dierucin is added, mixing them to obtain a W/O emulsion, and stirring further the W/O emulsion to form a W/O/W type multiple emulsion.

* * * * *